United States Patent [19]

Bellamy et al.

[11] Patent Number: 5,455,162
[45] Date of Patent: Oct. 3, 1995

[54] PROCESS FOR PRODUCING HEPARINASE WITH A BACILIUS STRAIN

[75] Inventors: Robert W. Bellamy, Zama; Kouki Horikoshi, Tokyo, both of Japan

[73] Assignee: Research Development Corporation of Japan, Tokyo, Japan

[21] Appl. No.: 285,383

[22] Filed: Aug. 3, 1994

Related U.S. Application Data

[62] Division of Ser. No. 799,597, Nov. 27, 1991, Pat. No. 5,362,645, which is a division of Ser. No. 440,061, Nov. 22, 1989, Pat. No. 5,145,778.

[30] Foreign Application Priority Data

Nov. 25, 1988 [JP] Japan ................................. 63-297807

[51] Int. Cl.$^6$ .............................. C12P 21/00; C12N 1/20
[52] U.S. Cl. ....................... 435/71.2; 435/252.5; 435/232
[58] Field of Search ............................... 435/71.2, 252.5, 435/232

[56] References Cited

U.S. PATENT DOCUMENTS 5,145,778  9/1992  Bellamy ..................................... 45/232
5,362,645  11/1994  Bellamy ............................... 435/252.5

FOREIGN PATENT DOCUMENTS

WO82/00659  3/1982  WIPO .

OTHER PUBLICATIONS

McLean et al., Proc. 8th Int. Symp. Glycocoujugates, vol. 1, pp. 73–74, 1985.
Hovingh et al., J. Biol. Chem., vol. 245, pp. 6170–6175, 1980.
Linker et al. In Methods in Enzymology, vol. 28, pp. 902–911, 1972.
Yang et al., J. Biol. Chem. 260(3): 1849–1857 (1985).
Karbassi et al., Chemical Abstracts 92(2): 229, abstract no. 176342b and Can. J. Microbiol. 26(3): 377–84 (1980).
Linhardt et al., Applied Biochemistry and Biotechnology 12(2): 135–176 (1986).
Nakamura et al., Journal of Clinical Microbiology 26(5): 1070–1071 (1988).
Böhmer et al., J. of Biol. Chem. 265(23): 13609–13617 (1990).
Nader et al., J. Biol. Chem. 265(26): 16807–16813 (1990).

Primary Examiner—Irene Marx
Attorney, Agent, or Firm—Pennie & Edmonds

[57] ABSTRACT

A newly discovered microorganism is described that was isolated in biologically pure culture from soil and designated Bacillus sp. strain BH100 (FERM BP-2613 (FERM P-10408)). This strain is used in a new process for production of extracellular heparinase. Additionally a new heparinase having an optimum temperature for activity in the range of 45° to 50° C. is disclosed.

1 Claim, 2 Drawing Sheets

PROCESS FOR PRODUCING HEPARINASE WITH A BACILIUS STRAIN

This is a division, of application Ser. No. 07/799,597, filed Nov. 27, 1991, now U.S. Pat. No. 5,362,645, which in turn is a divisional of application Ser. No. 07/440,061, filed on Nov. 22, 1989, currrently U.S. Pat. No. 5,145,778.

FIELD OF THE INVENTION

This invention relates to a biologically pure culture of a new microorganism belonging to the genus Bacillus characterized by the ability to degrade heparin and heparitin and by the production of extracellular heparinase. This invention further relates to a new extracellular heparinase and a process for producing the same.

BACKGROUND OF THE INVENTION

Heparinase is an enzyme which cleaves certain glycosidic linkages in heparin, a sulfated mucopolysaccharide having the major repeating unit: -4)-2-deoxy-2-sulfamino-α-D-glucopyranose-o-sulfate-( 1-4) -α-L-idopyranosyluronic acid-2-sulfate-( 1-. The products of this enzyme-activity are chain-shortened fragments of heparin. Heparinase also cleaves heparitin (otherwise known as heparin monosulfate or heparan sulfate), a sulfated mucopolysaccharide having a chemical structure similar to that of heparin, producing chain-shortened fragments of heparitin.

The substrate, heparin, is widely used as an anticoagulant drug and consequently heparinase has numerous applications in the study of heparin structure, investigation of the blood coagulation mechanism, and in bioassays for detection of heparin in body tissues and fluids. Heparinase also has use in the preparation of low molecular weight heparin fragments which have potential therapeutic value as anti-thrombotic or anti-tumour agents.

Heparinase derived from microorganisms of the genus Bacillus is new. Previously, enzymes capable of degrading heparin have been detected only in cultures of *Flavobacterium heparium*, Flavobacteriumsp. , Bacteroides sp. , *Bacteroides heparinolyticus*, Peptostrep-tococcus and Eubacterium. These heparinases are disclosed in Journal of Biochemistry [Vol. 233, p. 853 (1956)]; Experientia [Vol. 41, p. 1541 (1985)]; Matsumoto Dental School Journal (Japan) [Vol. 8, p. 15 (1982)]; Journal of Applied and Environmental Microbiology [Vol. 46, p. 1252 (1983)]; Journal of Clinical Microbiology [vol. 26, p. 1070 (1988)]; Journal of the South African Veterinary Association [Vol. 53, p. 214 (1982)].

The conventional heparinases all have one or more disadvantages, such as high cost of enzyme production and recovery, and low stability during purification, storage and use, which limit their practical use. At present, only the heparinase from *Flavobacterium heparinum* is commercially available.

PROBLEMS TO BE SOLVED BY THE PRESENT INVENTION

The conventional heparinases produced by bacteria of the genera Flavobacterium and Bacteroides are cell-bound enzymes that are not released into the culture medium. Consequently, recovery of such heparinase requires-cell disruption which adds considerable cost in the purification of the enzymes. An extracellular heparinase which is released into the fermentation culture medium does not require cell disruption for recovery and so is advantageous to achieve less costly enzyme recovery and purification.

Furthermore, the conventional heparinases are rapidly and Irreversibly inactivated at temperatures above 37° C. A more thermostable heparinase which retains activity at temperatures up to 50° C. is advantageous because :it exhibits greater stability during purification, storage and use at temperatures below 37° C. and it can be used at even higher temperatures, up to 50° C., to achieve more rapid reaction rates.

With the intention of creating a new heparinase, the present inventors tried to isolate a pure culture of a microorganism with properties including extracellular production of such a heparinase from nature. As a result of it, they discovered a new microorganism belonging to the genus Bacillus having the desirable properties described above which forms the basis of the present invention.

SUMMARY OF THE INVENTION

An object of the present invention lies in providing a new microorganism belonging to the genus Bacillus characterized by the ability to degrade heparin and heparitin and by the production of extracellular heparinase.

Another object of the present invention lies in providing a new heparinase (hereinafter, referred to as "the present enzyme")

A further object of the present invention lies in providing a process for production of the present enzyme.

The present invention provides a new microorganism belonging to the genus Bacillus characterized by the ability to degrade heparin and heparitin and the production of extracellular heparinase and to provide a new heparinase having an optimum temperature for activity in the range of 45 to 50° C., and a new process for production of said new heparinase characterized by culturing a microorganism belonging to the genus Bacillus producing extracellular heparinase and collecting said heparinase.

According to the present invention a useful new heparinase can be obtained.

BRIEF DESCRIPTION OF THE FIGURES

The present invention may be understood more fully by reference to the following detailed description of the invention, examples of specific embodiments of the invention and the appended figures in which.

DETAILED DESCRIPTION OF THE PREFERRED EMBODIMENT

ACQUISITION OF MICROORGANISM

Figure 1:
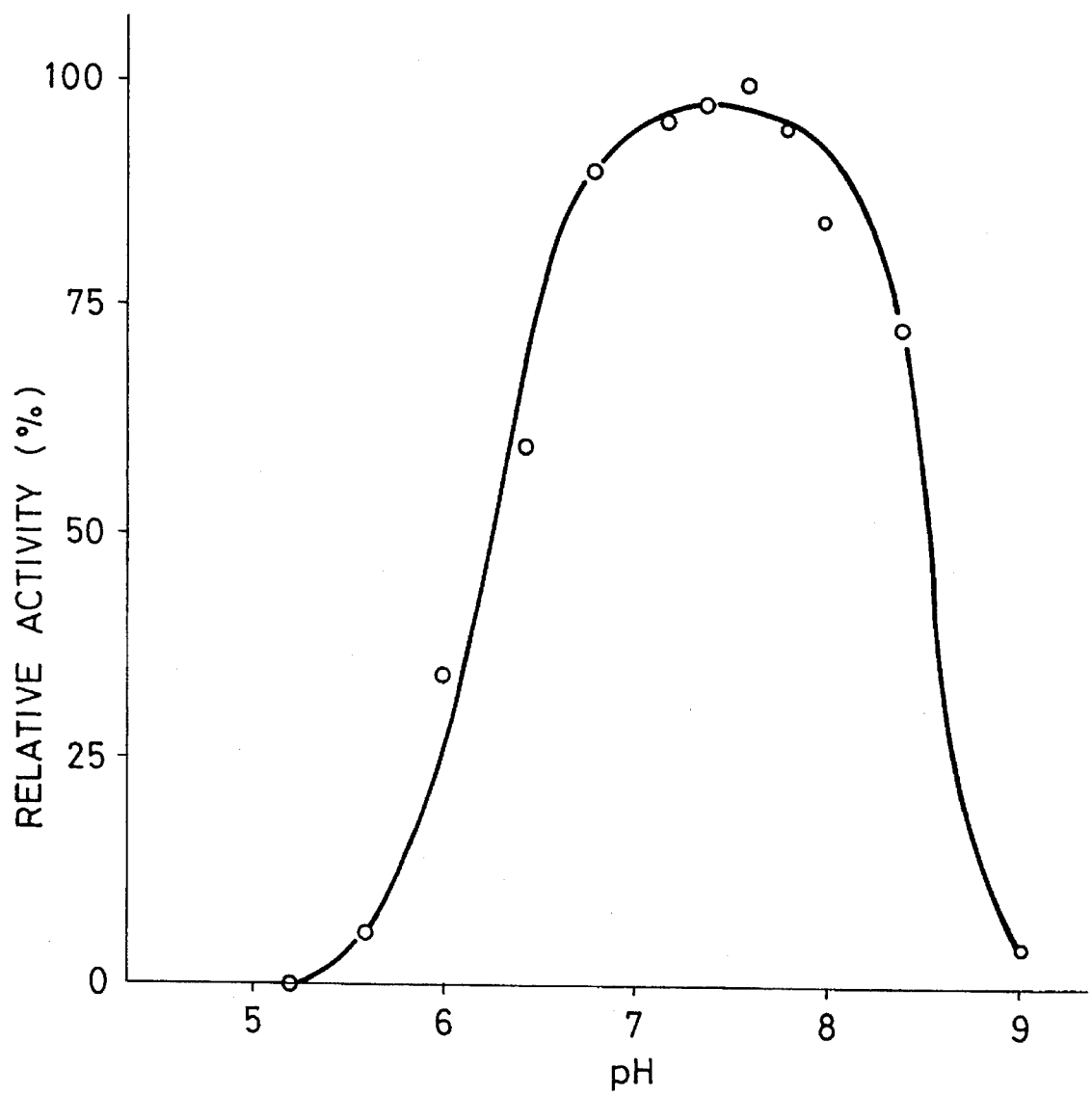
FIG. 1 is a graph showing the influence of pH on the activity of the present enzyme.

The present inventors isolated a large number of microorganisms from soils by selection for growth at 45° C. in a liquid medium containing mineral salts, trace amounts of vitamins, and heparin as the major nutrient. From those samples which exhibited evidence of microbial growth after one week of cultivation, the microorganisms were isolated in biologically pure form and tested for production of heparinase having activity at 45° C. Accordingly, one bacterial isolate was discovered which produced the desired heparinase activity and which furthermore released the heparinase into the culture medium. This new heparinase-producing isolate was designated strain BH100.

The taxonomic properties of strain BH100 were examined in accordance with methods described in Bergey's Manual of Systematic Bacteriology, Volume 2, and the strain was found to be Gram-positive, spore-forming, rod-shaped, facultatively anaerobic, motile, catalase-positive and had a growth temperature range of 20° to 55° C. Based on these characteristics, it was determined that the strain was a microorganism belonging to the genus Bacillus.

In comparison with known species of the genus Bacillus, the taxonomic properties of strain BH100 were found to resemble those of the species *Bacillus circulans* in some respects. However, strain BH100 differed from *Bacillus circulans* in several important properties, most notably, growth at 55° C., pit in VP-broth above 6.0, guanine plus cytosine content of DNA within the range 56–58% and the ability to degrade heparin and heparitin. Accordingly, strain BH100 was judged to be a new species, different from known species belonging to the genus Bacillus.

The present inventors deposited strain BH100 in the Fermentation Research Institute, Agency of Industrial Science and Technology of Japan where the strain was given the deposit number (FERM BP-2613 (FERM P-10408)). The taxonomic properties of this strain are given in Table 1.

TABLE 1

TAXONOMIC PROPERTIES OF BACILLUS STRAIN BH100

1. Morphological Properties

| | |
|---|---|
| Gram's stain | positive |
| Cell size | 0.6–0.8 μm × 3–6 vm |
| Spore shape | cylindrical |
| Sporangium swollen | positive |
| Spore position | terminal |
| Parasporal crystals | negative |
| Motility | positive |

2. Growth Properties

| | |
|---|---|
| Aerobic growth | positive |
| Anaerobic growth | positive |
| Growth temperature | |
| maximum | 55° C. |
| minimum | 20° C. |
| optimum | 45° C. |
| Growth with lysozyme present (0.001%) | positive |
| Growth with azide present (0.02%) | negative |
| Growth with NaCl | |
| at 2% | positive |
| at 5% | negative |
| at 7% | negative |
| at 10% | negative |
| Growth at pH 6.8 (Nutrient Broth) | positive |
| at pH 5.7 (Sabouraud Medium) | positive |
| Requirement for NaCl and KCl | negative |
| Growth factors required | none |

3. Biochemical Properties

| | |
|---|---|
| Catalase | positive |
| Voges-Proskauer test | negative |
| pH in V-P broth | 6.5–7.0 |
| Acid from | |
| D-ribose | positive |
| D-xylose | positive |
| L-rhamnose | positive |
| D-galactose | positive |
| D-fructose | positive |
| D-arabinose | positive |

TABLE 1-continued

TAXONOMIC PROPERTIES OF BACILLUS STRAIN BH100

| | |
|---|---|
| L-arabinose | positive |
| raffinose | positive |
| D-mannose | positive |
| maltose | positive |
| sucrose | positive |
| lactose | positive |
| D-glucose | positive |
| D-trehalose | positive |
| glycerol | positive |
| D-mannitol | positive |
| sorbitol | negative |
| m-erythritol | positive |
| inositol | positive |
| adonitol | positive |
| Gas from fermented carbohydrates | negative |
| Indole production | negative |
| Dihydroxyacetone production | negative |
| Crystalline dextrins production | negative |
| Nitrate reduction | negative |
| Utilization of citrate | positive |
| propionate | negative |
| Decomposition of tyrosine | negative |
| Hydrolysis of starch | negative |
| casein | negative |
| Degradation of heparin | positive |
| heparitin | positive |
| chondroitin A | positive |
| chondroitin B | positive |
| chondroitin C | positive |
| hyaluronic acid | positive |
| polygalacturonic acid | negative |
| Guanine plus cytosine content in DNA | 57 mol % |

As a medium for culturing of strain BH100, an ordinary medium containing a carbon source, nitrogen source, and inorganic salts is used. As a carbon source, any of those which can be assimilated can be used, for example, D-glucose, maltose, D-xylose, sucrose, heparin, citrate, succinate, glutamate, tryptone, or peptone can be enumerated as typical examples. As a nitrogen source, various conventional materials can be used, for example, yeast extract, peptone, meat extract, corn steep liquor, amino acid solution, etc. or inorganic nitrogen such as ammonium sulfate, ammonium chloride, etc. can be enumerated as readily available sources. Furthermore, in addition to such carbon and nitrogen sources as above, it is possible to add various salts in use commonly, for example, inorganic salts such as as magnesium sulfate, magnesium chloride, potassium phosphate, sodium phosphate, potassium chloride, calcium chloride, etc. Vitamins and other growth factors are not essential but it is possible to add such materials as folic acid, calcium pantothenate, biotin, riboflavin, thiamine, etc. It is further possible to add a gelling agent such as agar, gelatin, gellan gum, etc. if desired. The medium is adjusted to a final pH of 5.5 to 8.5, preferably pH 6.5 to 8.0, by addition of an acid or base as is appropriate.

Heparinase synthesis by strain BH100 is induced by the presence of heparin in the culture medium. For production of heparinase arin is added to the culture medium at 0.05 to 10.0 grams per liter, preferably 1.0 to 2.0 grams per liter.

As a specific example of a suitable medium, a liquid medium containing (per liter) 10 g of triptone, 1.0 g of yeast extract, 3.5 g of $K_2HPO_4$, 2.0 g of $MgCl_2.6H_2O$, and 1.0 g of heparin and having the pH adjusted to pH 8.0 with NaOH can be enumerated.

The strain BH100 is cultured preferably under aerobic conditions at 30° to 50° C.

ACQUISITION OF THE PRESENT ENZYME

The strain producing the present enzyme is cultured in any suitable medium, such as described above, containing heparin as inducer at 0.05 to 10 grams per liter, preferably at 1.0 to 2.0 grams per liter, and incubated aerobically at 30° to 50° C. for 12 to 72 hours.

Isolation and purification of the present enzyme can be carried out, for example, as follows. Cells are removed from the liquid culture medium which contains most of the heparinase activity by centrifugation, microfiltration, or other conventional methods. At this stage, the crude heparinase can be concentrated using conventional methods such as precipitation with ammonium sulfate or acetone, dialysis with polyethylene glycol, or ultrafiltration. Alternatively, the crude heparinase can be further processed without such a concentration step. The crude heparinase activity is applied to chromatographic media such as usual ion-exchange and gel filtration media, and/or, fractionated by various other conventional methods well known to those skilled in the art of enzyme purification such as chromato-focusing, preparative isoelectofocusing, electophoresis, etc., thereby obtaining the present enzyme.

A preferable method for acquiring the present enzyme can be exemplified as follows. Bacillus sp. strain BH100 is cultured in a suitable medium as indicated above, containing heparin as inducer at a concentration of 1 to 2 grams per liter, and incubated aerobically at 40° to 45° C. for 36 to 40 hours. The obtained culture is centrifuged at 8,000×g at 10° C. for 30 minutes so as to remove the cells from the culture supernatant. Solid ammonium sulfate is added to the culture supernatant to 70% of saturation and the solution is let stand at 5° C. for 3 hours so as to form a precipitate containing the crude heparinase.

The precipitate is collected by centrifugation at 8000×g at 10° C. for 30 minutes and dissolved in 10 mM HEPES buffer pH 7.8. The crude heparinase solution is dialysed for 24 hours at 5° C. against 100 volumes (2 changes) of 10 mM HEPES buffer plt 7.8. The dialysate is centrifuged at 12000×g at 10° C. for 30 minutes and the precipitated protein is discarded. The crude heparinase solution is loaded onto a column of DEAE- TOYOPEARL equilibrated with 10 mM HEPES buffer pH 7.8 and eluted with the same buffer. The eluate is collected as a single active fraction and this enzyme solution is loaded onto a column of CELLULOFINE-SULFATE equilibrated with the same buffer.

The enzyme is eluted with a linear concentration gradient of 0 to 0.3M NaCl in 10 mM HEPES buffer, pH 7.8. The active fractions which are eluted at about 0.19M NaCl are collected and concentrated by ultrafiltration using an Amicon PM10 membrane. Thus treated enzyme solution is subjected to gel filtration using a column of SHODEX WS-2003 equilibrated with 100 mM NaCl in 50 mM HEPES buffer pH 7.4 and eluted with the same buffer. The active fractions thus obtained are combined and contain only the purified heparinase as indicated by a single protein band upon examination by sodium dodecyl sulfate-polyacrylamide gel electrophoresis.

PROPERTIES OF THE PRESENT ENZYME.

Figure 2:
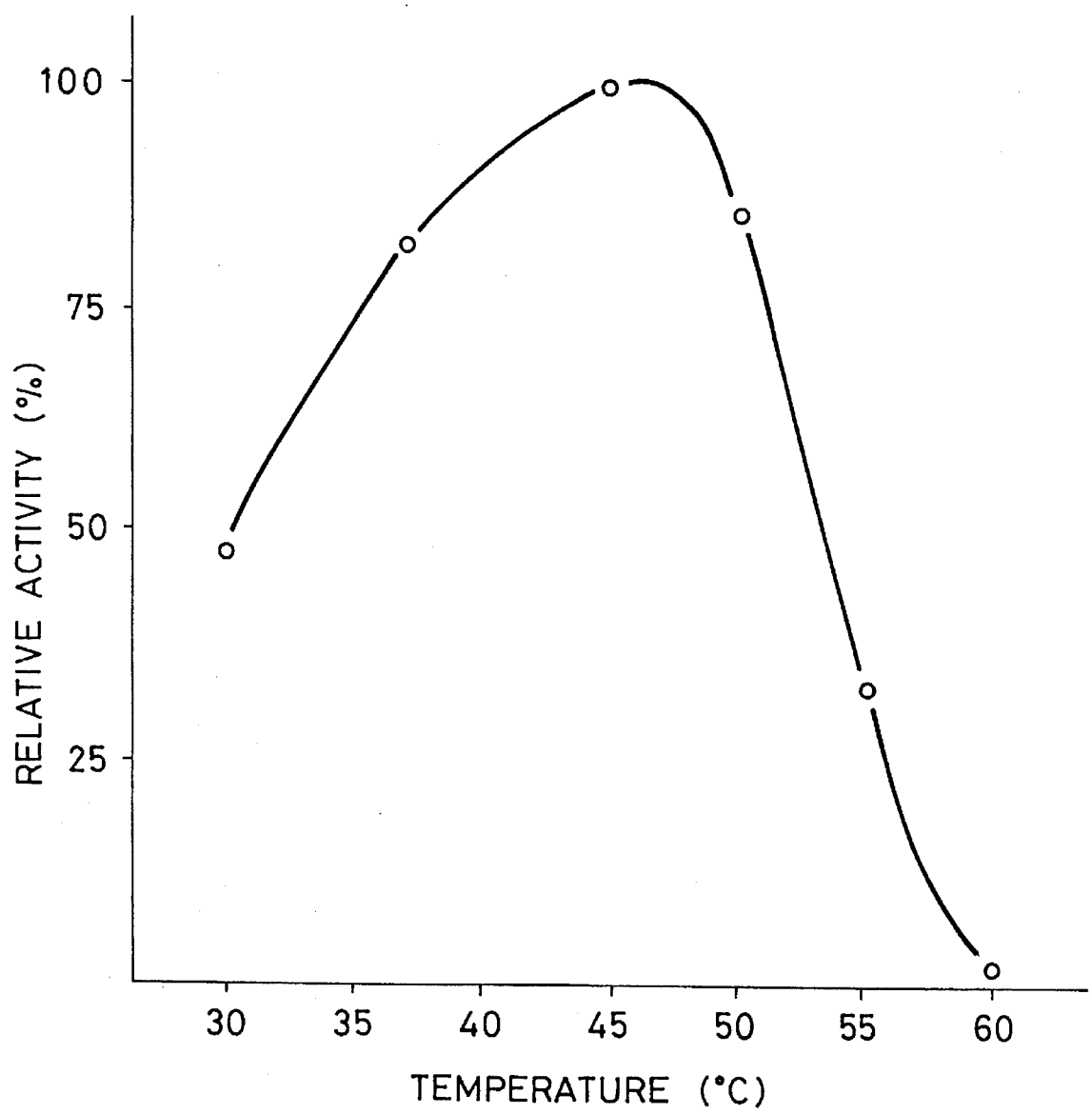
FIG. 2 is a graph showing the influence of temperature on the activity of the present enzyme.

The enzymological properties of the present enzyme produced according to the present process are as follows:
(a) Action:
Catalyses the eliminative cleavage of heparin and heparitin and thereby produces chain-shortened fragments, of heparin and heparitin, respectively, which exhibit ultraviolate absorbance at 232 nm.
(b) Substrate specificity:
Cleaves heparin and heparitin but not chondroitin A, chondroitin B, chondroitin C, hyaluronic acid, dextran sulfate, and polygalacturonic acid.
(c) Optimum pH and stable range:
optimum pH for activity is 7.2 to 7.8 as shown in FIG. 1. Stable within the pH range of pH 7.0 to 8.0 under the condition of 24 hour retention of activity at 30° C.
(d) Thermostability:
At pH 7.4 and in the presence of 5.0 mM $CaCl_2$, about 100% of the enzymatic activity remains after 30 minutes heating at 45° C. and about 10% of the activity remains after 3 hours heating at 45° C. Calcium ions are required for stability.
(e) Optimum temperature range:
Optimum temperature for activity in the presence of mM $CaCl_2$ is 45° C. (30 minute assay; FIG. 2) or 50° C. (10 minute assay), depending upon the duration of the assay period used.
(f) Effect of inorganic ions:
The enzymetic activity is increased by about 50% in the presence of 2 5 mM chloride salts of $Ca^{2+}$, $Mg^{2+}$ or $Ba^{2+}$. The activity is increased by about 100% in the presence of an optimum concentration of 5 mM $Ca^{2+}$. The activity is lowered in the presence of 0.5 mM chloride salts of $Co^{2+}$, $Zn^{2+}$, $Cu^{2+}$ $Ni^{2+}$ and $Pb^{2+}$ by about 38%, 66%, 90% 80%, and 100%, respectively. Chloride salts of $Fe^{2+}$, $Mn^{2+}$ and $Li^{2+}$ ions at 2.5 mM do not influence the activity. NaCl inhibits the activity to the extent of about 10%, 44% 88% and 100% at concentrations of 30 mM, 100 mM, 200 mM, 300 mM respectively.
(g) Molecular weight:
The molecular weight of the present enzyme is about 120000 as estimated by sodium dodecyl sulfate-polyacrylamide gel electrophoresis using a 4 to 20% linear gradient gel with reference to molecular weight standard proteins.

Comparison of physiochemical properties of the present enzyme with the conventionally known heparinases are shown in Table 2.

TABLE 2

COMPARISON OF HEPARINASE FROM BACILLUS BH100 WITH KNOWN HEPARINASES

|  | *Flavobacterium heparinum* | *Bacteroides heparinolyticus* | *Bacillus* BH100 |
|---|---|---|---|
| MECHANISM | eliminase | eliminase | eliminase |
| LOCATION | cell-bound | cell-bound | extracellular |
| Mr | 43000 | 63000 | 120000 |
| TEMP OPTIMUM | 30 to 37° C. | 30 to 37° C. | 45 to 50° C. |
| STABLE | 1 hr at 30° C. | 1 hr at 37° C. | 1 hr at 45° C. |

TABLE 2-continued

COMPARISON OF HEPARINASE FROM BACILLUS BH100 WITH KNOWN HEPARINASES

|  | *Flavobacterium heparinum* | *Bacteroides heparinolyticus* | Bacillus BH100 |
|---|---|---|---|
| REACTION DENATURATION | 5 min at 45° C. | 5 min at 45° C. | 5 min at 60° C. |
| pH OPTIMUM | 6.5 | 6.5 | 7.5 |
| ACTIVATION | 0.1 M NaCl | 1 mM $Fe^{2+}$ | 5 mM $Ca^{2+}$ $Mg^{2+}$ $Ba^{2+}$ |

Methods of measuring and indicating the activity of the present enzyme are as follows.

(h) toluidene Blue Metachromatic Assay:

Reaction mixtures containing 20 μl of the present enzyme solution (suitably diluted), 80μl of 50 mM HEPES buffer, pH, 7.4 and 20 μl of 100 ug per ml of heparin (sodium salt) are sealed to prevent evaporation and held at 45° C. for 30 minutes. Then 20 μl of 0,025 mg/ml toluidene blue solution is added and the absorbance of the solution is determined at 620 nm. The total amount of heparin remaining in the reaction mixtures is calculated from their absorbance by reference to a series of standard solutions of known heparin concentration. One Unit of enzyme activity is taken as the amount required to degrade 1.0 mg of heparin per hour at 45° C.

(i) Ultraviolet Absorbance Assay:

Reaction mixtures containing 20 μl of the present enzyme (suitably diluted) and 50 μl of 10 mg/ml heparin in 50 mM HEPES buffer, pH 7.4, are held at 45° C. for 30 minutes. Thereafter, the reaction is discontinued by addition of 2.0 ml of 20 mM KCl-HCl solution, pH 2.0 and the absorbance of the solution is determined at 232 nm. One International Unit. (I.U.) of enzyme activity is taken as the amount of enzyme required to generate 1 micromole of double bonds per minute at 45° C., based on a molar extinction coefficient of 5100 $cm^{-1}M^{-1}$ for the degradation products.

The following examples are merely illustrative of the invention, and are not intended to limit the same.

EXAMPLES

Example 1

A newly discovered strain, designated Bacillus sp. strain BH100 (FERM BP-2613 (FERM P-10408)), was isolated from soil as follows. About 0.1 g of soil sample was added to 1.5 ml of medium which consisted of (per liter): 2.0 g of heparin, 0.35 g of $K_2HPO_4$, 0.27 g of $NH_4Cl$, 0.2 g of $MgCl_2.6H_2O$, 0,001 g of each of lysine, histidine, and methionine, 0.0025 mg of ferrous citrate, 0.1 ml of trace element solution [containing (per liter): 0.12 g of $ZnSO_4$, 0.5 g of $MnSO_4$, 0.13 g of $H_3BO_3$, 0.004 g of $CuSO_4$, 0.006 g of $NA_2MoO_4$, and 0.012 g of $COCl_2.6H_2O$], and 0.1 ml of vitamin solution containing (per liter): 10 mg each of folic acid and biotin, 25 mg each of riboflavin, thiamine, nicotine acid, calcium pantothenate and para-aminobenzoic acid, and 50 mg of pyridoxine hydrochloride]. The cultures were held in sterile 24-well microtiker trays, sealed with plastic wrap to minimize evaporation, at 45° C., without shaking. From those samples which exhibited evidence of microbial growth after one week of cultivation, the microorganisms were isolated in biologically pure form by repeated subculture of cells on a solid medium containing (per liter): 2.0 g of heparin, 0.1 g of $K_2HPO_4$, 1.0 g of $MgCl_2.6H_2O$ and 8.0 g of gellan gum, at pH 8.0, with incubation at 45° C.

Example 2

The biologically pure isolates obtained as indicated in Example 1 were tested for production of heparinase activity by culturing the cells in 20 ml of liquid medium containing (per liter): 14 g of tryprone, 1.0 g of yeast extract, 3.5 g of $K_2HPO_4$, 2 g of $MgCl_2$, and 1.0 g of heparin, adjusted to pH 8.0 with NaOH. The cultures were incubated at 45° C., with rotary shaking at 65 rpm. After 72 hours of cultivation, the cells were collected by centrifugation at 8000×g for 20 minutes and the supernatant was tested for residual heparin by the Toluidene Blue Metachromatic Assay. In the culture containing Bacillus sp. strain BH100 (FERM BP-2613 (P-10408)), the amount of heparin remaining in the culture supernatant was determined to be zero mg per ml. Heparinaseactivity was assayed by the Toluidene Blue Metachromatic Assay at 45° C. and the culture supernatant was found to contain 0.074 units of heparinase per ml.

Example 3

Bacillus sp. strain BH100 (FERM BP-2613 (P-10408)) was cultured in 20 ml of medium containing (per liter): 7.0 g of HEPES buffer, 2.0 g of yeast extract, 0.5 g of $K_2HPO_4$, 1.0 g of $MgCl_2$, 1.0 g of heparin, and 10 g of carbon source as indicated below, adjusted to pH 8.0 with NaOlt. The cultures were incubated at 45° C. with rotary shaking at 65 rpm. After 40 hours, 64 hours and 72 hours of cultivation, 1.0 ml samples were removed from each culture, the cells were collected by centrifugation, and the culture supernatants were tested for heparinase activity by the Toluidene Blue Metachromatic assay as indicated in Table 3.

TABLE 3

| | HEPARINASE ACTIVITY | | |
|---|---|---|---|
| Carbon source | Heparinase 40 h | Activity 64 h | (Units per ml) 72 h |
| glutamate | 0 | 0 | 0.080 |
| proline | 0.138 | 0.104 | 0.034 |
| succinate | 0.144 | 0.096 | 0.026 |
| glycerol | 0 | 0.042 | 0.042 |
| glycolate | 0 | 0.026 | 0.080 |
| acetate | 0.140 | 0.076 | 0.098 |
| xylose | 0 | 0.068 | 0.062 |

Example 4

Induction of heparinase synthesis by Bacillus sp. strain BH100 (FERM BP-2613 (FERM P-10408)) was examined as follows. Strain BH100 was cultured in 20 ml of liquid medium containing (per liter): 10 g of tryptone, 1.0 g of yeast extract, 3.5 g of $K_2HPO_4$, 2.0 g of $MgCl_2.6H_2O$, and chondroitin A, chondroitin B, Chondroitin C, hyaluronic acid, polygalacturonic acid, dextran sulfate, glucosamine or glucuronic acid, each at 1 g per liter, or heparin at the concentration as indicated below. Cultures were incubated at 45° C. with rotary shaking at 65 rpm. After 36 hours of cultivation, the cells were removed by centrifugation and the culture supernatant was further processed as follows. Solid ammonium sulfate was added to 70% of saturation and the solution was held at 5° C. for 3 hours to form a precipitate. The precipitate was collected by centrifugation at 8000×g at 10° C. for 30 minutes and was dissolved in 2.0 ml of 20 mM HEPES buffer, pH 7.4. This solution was dialysed for 16 hours at 4° C. in 4 liters of 20 mM HEPES pH 7.4, then heparinase activity was assayed at 45° C. using the Ultraviolet Absorbance Assay method. The results are summarized in Table

TABLE 4

INDUCTION OF HEPARINASE

| Potential Inducer | | Heparinase Activity |
|---|---|---|
| | mg/ml | I.U./liter |
| none | | 0 |
| heparin | 0.1 | 0.32 |
| heparin | 0.2 | 1.39 |
| heparin | 0.5 | 3.10 |
| heparin | 1.0 | 5.45 |
| heparin | 2.0 | 8.33 |
| heparin | 5.0 | 5.66 |
| others* | | 0 |

*Others respresents chondroitins A, B or C, hyaluronic acid, polygalacturonic acid, dextran sulfate, glucosamine, or glucuronic acid.

As illustrated by the above data, heparinase synthesis by Bacillus sp. strain BH100 is induced by the presence of heparin in the growth medium. Production of the enzyme is not induced by the presence of chondroitins A, B or C, hyaluronic acid, polygalacturonic acid, dextran sulfate, glucosamine, or glucuronic acid.

Example 5

Purification of the heparinase is illustrated as follows. Bacillus sp. strain B100 (FERM BP-2613 (FERM P-10408)) was cultured from a 5% inoculum in 6.0 liters of liquid medium containing (per liter): 10 g of tryptone, 1.0 g of yeast extract, 3.5 g of $K_2$ g of $MgCl_{2.6}$ $H_2O$, and 2.0 g of heparin, adjusted to pH 7.4 with NaOH, and incubated aerobically at 40° C. for 36 hours. The obtained culture was centrifuged at 8000×g at 10° C. for 30 minutes so as to remove the cells form the culture supernatant. An estimated 14% of the total heparinase activity was cell-bound and discarded. Solid ammonium sulfate (2652 g) was added to the culture supernatant to attain 70% of saturation and the solution was allowed to stand at 5° C. for 3 hours so as to form a precipitate containing the crude heparinase. The precipitate was collected by centrifugation at 8000×g at 10° C. for 30 minutes and dissolved in 50 ml of 10 mM HEPES buffer pH 7.8. The crude heparinase solution was dialysed for 24 hours at 5° C. against 10 liters (2 changes of 5 liters) of 10 mM HEPES buffer pH 7.8. The dialysate was centrifuged at 12000×g at 10° C. for 30 minutes and the precipitated protein was discarded. Further purification was performed at room temperature, that is, at about 22° C. Heparinase activity was monitored at each step using the Ultraviolet Absorbance Assay. The crude heparinase solution was loaded onto a column of DEAE-TOYOPEARL equilibrated with 10 mM HEPES buffer pH 7.8 and eluted with the same buffer. The eluate was collected as a single active fraction and this enzyme solution was loaded onto a column of CELLULOFINE-SULFATE equilibrated with the same buffer. The enzyme was eluted with a linear concentration gradient of 0 to 0.3M NaCl in 10 mM HEPES buffer, pH 7.8. The active fractions which eluted at about 0.19M NaCl were collected and concentrated by ultrafiltration using an Amicon PM10 membrane. Thus treated enzyme solution was subjected to gel filtration using a column of SHODEX WS-2003 equilibrated with 100 mM NaCl in 50 mM HEPES buffer pit 7.4 and eluted with the same buffer. The active fractions thus obtained were combined and found to contain only the purified heparinase as indicated by a single protein band upon examination by sodium dodecyl sulfate-polyacrylamide gel electrophoresis. The results of the purification are summarized in Table 5.

TABLE 5

| Fraction | Total Protein (mg) | Activity Total (I.U.) | Specific Activity (I.U/mg protein) |
|---|---|---|---|
| Supernatant | 1080 | 16.3 | 0.015 |
| Ammonium Sulfate, (Dialysate) | 818 | 13.7 | 0.017 |
| DEAE-TOYOPEARL | 109 | 20.0 | 0.183 |
| CELLULOFINE-SULFATE | 1.53 | 4.28 | 2.80 |
| SHODEX WS-2003 | 0.44 | 2.09 | 4.75 |

What is claimed is:

1. A process for producing heparinase comprising culturing in an aqueous nutrient medium the microorganism Bacillus sp. BH100, BP-2763, wherein the extracellular heparinase produced has a molecular weight of 120,000 daltons as determined by SDS PAGE, and the physiochemical properties of optimum activity in the pH range of 7.2–7.8 and the temperature range of 45°– 50° C., a pI of 6.6 and stability of at least 30 minutes at 45° C. in the presence of calcium, and recovering the heparinase produced from the culture medium.

* * * * *

UNITED STATES PATENT AND TRADEMARK OFFICE
CERTIFICATE OF CORRECTION

PATENT NO. : 5,455,162

DATED : October 3, 1995

INVENTOR(S) : Wayne Robert Bellamy and Kouki Horikoshi

It is certified that error appears in the above-identified patent and that said Letters Patent is hereby corrected as shown below:

On the title page:

In item [54] the word "BACILIUS" is incorrect. The title should read: PROCESS FOR PRODUCING HEPARINASE WITH A BACILLUS STRAIN

In item [75] the name of the first inventor is incorrect. The Inventors are: Wayne Robert Bellamy, Zama; Kouki Horikoshi, Tokyo, both of Japan Signed and Sealed this Thirtieth Day of January, 1996

Attest:

BRUCE LEHMAN

Attesting Officer

Commissioner of Patents and Trademarks